US011440030B2

(12) United States Patent
Hogan et al.

(10) Patent No.: US 11,440,030 B2
(45) Date of Patent: Sep. 13, 2022

(54) METHOD FOR PRODUCING AN APERTURE PLATE

(71) Applicant: Stamford Devices Limited, Dangan (IE)

(72) Inventors: Brendan Hogan, Gort (IE); Hong Xu, Redwood City, CA (US)

(73) Assignee: Stamford Devices Limited, Galway (IE)

( * ) Notice: Subject to any disclaimer, the term of this patent is extended or adjusted under 35 U.S.C. 154(b) by 48 days.

(21) Appl. No.: 16/358,338

(22) Filed: Mar. 19, 2019

(65) Prior Publication Data

US 2019/0210044 A1    Jul. 11, 2019

Related U.S. Application Data

(63) Continuation of application No. 14/719,036, filed on May 21, 2015, now Pat. No. 10,279,357.

(Continued)

(51) Int. Cl.
*B05B 17/06* (2006.01)
*B05B 1/02* (2006.01)
(Continued)

(52) U.S. Cl.
CPC ............ *B05B 1/02* (2013.01); *B05B 17/0638* (2013.01); *B05B 17/0653* (2013.01); *C25D 1/08* (2013.01);
(Continued)

(58) Field of Classification Search
CPC ... B05B 1/02; B05B 17/0638; B05B 17/0653; B05B 17/0646; C25D 1/08; C25D 1/10;
(Continued)

(56) References Cited

U.S. PATENT DOCUMENTS 2,226,706 A    12/1940  Cawein
3,130,487 A     4/1964  Mears
(Continued)

FOREIGN PATENT DOCUMENTS

CN    1149907 A    5/1997
DE    1948135 A1   4/1971
(Continued)

OTHER PUBLICATIONS

International Search Report and Written Opinion for International Application No. PCT/EP2013/060803, dated Jun. 11, 2014, 11 pages.

(Continued)

*Primary Examiner* — Tuongminh N Pham
(74) *Attorney, Agent, or Firm* — Bookoff McAndrews, PLLC

(57) ABSTRACT

An aperture plate is manufactured by plating metal around a mask of resist columns having a desired size, pitch, and profile, which yields a wafer about 60 μm thickness. This is approximately the full desired target aperture plate thickness. The plating is continued so that the metal overlies the top surfaces of the columns until the desired apertures are achieved. This needs only one masking/plating cycle to achieve the desired plate thickness. Also, the plate has passageways formed beneath the apertures, formed as an integral part of the method, by mask material removal. These are suitable for entrainment of aerosolized droplets exiting the apertures.

14 Claims, 2 Drawing Sheets

Related U.S. Application Data

(60) Provisional application No. 62/002,435, filed on May 23, 2014.

(51) Int. Cl.

| | | |
|---|---|---|
| *C25D 1/08* | (2006.01) | |
| *C25D 7/04* | (2006.01) | |
| *B05B 17/00* | (2006.01) | |
| *A61M 11/00* | (2006.01) | |
| *A61M 15/00* | (2006.01) | |

(52) U.S. Cl.
CPC .............. *C25D 7/04* (2013.01); *A61M 11/005* (2013.01); *A61M 15/0085* (2013.01); *A61M 2207/00* (2013.01)

(58) Field of Classification Search
CPC ... C25D 7/04; C25D 3/00–3/56; C25D 1/708; B41J 2/162; B41J 2/164; A61M 11/005; A61M 15/085; A61M 2207/00; A61M 11/003
See application file for complete search history.

(56) References Cited

U.S. PATENT DOCUMENTS

| | | | |
|---|---|---|---|
| 3,325,319 A | 6/1967 | Frantzen | |
| 4,184,925 A | 1/1980 | Kenworthy | |
| 4,379,737 A | 4/1983 | Mearig | |
| 4,430,784 A | 2/1984 | Brooks et al. | |
| 4,628,165 A | 12/1986 | Nobel et al. | |
| 4,773,971 A | 9/1988 | Lam et al. | |
| 4,839,001 A | 6/1989 | Bakewell | |
| 4,844,778 A | 7/1989 | Witte | |
| 4,849,303 A | 7/1989 | Graham et al. | |
| 4,972,204 A | 11/1990 | Sexton | |
| 5,152,456 A | 10/1992 | Ross et al. | |
| 5,164,740 A | 11/1992 | Ivri | |
| 5,180,482 A | 1/1993 | Abys et al. | |
| 5,373,629 A | 12/1994 | Hupe et al. | |
| 5,443,713 A | 8/1995 | Hindman | |
| 5,487,378 A | 1/1996 | Robertson et al. | |
| 5,560,837 A * | 10/1996 | Trueba .................... B41J 2/162 205/127 | |
| 5,565,113 A | 10/1996 | Hadimiouglu et al. | |
| 5,586,550 A | 12/1996 | Ivri et al. | |
| 5,646,662 A | 7/1997 | Kitahara | |
| 5,685,491 A | 11/1997 | Marks et al. | |
| 5,758,637 A | 6/1998 | Ivri et al. | |
| 5,766,441 A | 6/1998 | Arndt et al. | |
| 5,837,960 A | 11/1998 | Lewis et al. | |
| 5,899,390 A | 5/1999 | Arndt et al. | |
| 5,921,474 A | 7/1999 | Zimmermann et al. | |
| 5,976,342 A | 11/1999 | Arndt et al. | |
| 6,050,507 A | 4/2000 | Holzgrefe et al. | |
| 6,074,543 A | 6/2000 | Yoshihira et al. | |
| 6,205,999 B1 | 3/2001 | Ivri et al. | |
| 6,230,992 B1 | 5/2001 | Arndt et al. | |
| 6,235,177 B1 | 5/2001 | Borland et al. | |
| 6,310,641 B1 | 10/2001 | Mrvos et al. | |
| 6,357,677 B1 | 3/2002 | Ren et al. | |
| 6,586,112 B1 | 7/2003 | Te | |
| 6,605,866 B1 | 8/2003 | Crowley et al. | |
| 6,773,094 B2 | 8/2004 | Linliu et al. | |
| 7,066,398 B2 | 6/2006 | Borland et al. | |
| 7,104,475 B2 | 9/2006 | Goenka et al. | |
| 7,259,640 B2 | 8/2007 | Brown et al. | |
| 7,442,303 B2 | 10/2008 | Jacobson | |
| 8,398,001 B2 | 3/2013 | Borland et al. | |
| 2001/0013554 A1 | 8/2001 | Borland et al. | |
| 2002/0063751 A1 | 5/2002 | Aizawa et al. | |
| 2002/0157956 A1 | 10/2002 | Ikeda | |
| 2003/0231227 A1 | 12/2003 | Kim | |
| 2004/0008435 A1 | 1/2004 | Takahashi et al. | |
| 2004/0035413 A1 | 2/2004 | Smaldone et al. | |
| 2005/0263608 A1 | 12/2005 | Ivri | |
| 2006/0055739 A1 | 3/2006 | Kim et al. | |
| 2006/0086689 A1 | 4/2006 | Raju et al. | |
| 2006/0203036 A1 | 9/2006 | Sexton et al. | |
| 2007/0023547 A1 | 2/2007 | Borland et al. | |
| 2007/0212653 A1 | 9/2007 | Hori | |
| 2007/0277816 A1 | 12/2007 | Morrison et al. | |
| 2008/0023572 A1 | 1/2008 | Clark | |
| 2009/0053174 A1 | 2/2009 | Kaneko et al. | |
| 2009/0215264 A1 * | 8/2009 | Yu .................... H01L 21/76856 438/675 | |
| 2010/0055045 A1 | 3/2010 | Gerhart et al. | |
| 2010/0200408 A1 * | 8/2010 | Liu ......................... C25D 9/08 205/50 | |
| 2010/0282247 A1 | 11/2010 | Kadrichu et al. | |
| 2010/0319694 A1 | 12/2010 | Cook et al. | |
| 2012/0309125 A1 * | 12/2012 | Aksu .................. H01L 31/0322 438/57 | |
| 2013/0043127 A1 * | 2/2013 | Graham .................. C25D 1/10 204/279 | |
| 2013/0252020 A1 | 9/2013 | Hradil | |
| 2013/0334338 A1 | 12/2013 | Hogan | |
| 2013/0334339 A1 | 12/2013 | Xu | |
| 2015/0101596 A1 | 4/2015 | Hogan | |
| 2015/0336115 A1 | 11/2015 | Hogan et al. | |
| 2016/0130715 A1 | 5/2016 | Xu | |

FOREIGN PATENT DOCUMENTS

| | | |
|---|---|---|
| DE | 2050285 A1 | 5/1972 |
| DE | 19527846 | 1/1997 |
| EP | 0683048 A2 | 11/1995 |
| EP | 1199382 A1 | 4/2002 |
| EP | 1810743 | 7/2007 |
| EP | 2204238 A1 | 7/2010 |
| GB | 2240494 A | 8/1991 |
| GB | 2524337 A | 9/2015 |
| JP | 4183892 | 6/1992 |
| JP | H04-322290 | 11/1992 |
| JP | H05-239682 | 9/1993 |
| JP | H05-74669 | 10/1993 |
| JP | 10-507243 | 7/1998 |
| JP | 10-228114 | 8/1998 |
| JP | 11138827 | 5/1999 |
| JP | 2002019125 | 1/2002 |
| JP | 2002-166541 | 6/2002 |
| JP | 2002187374 A | 7/2002 |
| JP | 2002-289097 | 10/2002 |
| JP | 2004-290426 A | 10/2004 |
| JP | 2006-056151 | 3/2006 |
| JP | 20060297688 | 11/2006 |
| JP | 7-329304 | 12/2007 |
| JP | 2008-545525 | 12/2008 |
| JP | 2010-540526 A | 12/2010 |
| JP | 2009-195669 A | 9/2015 |
| RU | 2078405 | 4/1997 |
| WO | WO 91/03920 A2 | 3/1991 |
| WO | WO 01/18280 A1 | 3/2001 |
| WO | WO 01/071065 | 3/2001 |
| WO | WO 2006/127181 | 11/2006 |
| WO | WO 2009/042187 A1 | 4/2009 |
| WO | WO 2010/134967 A1 | 11/2010 |
| WO | WO 2011/039233 A1 | 4/2011 |
| WO | WO 2011/083380 A1 | 7/2011 |
| WO | WO 2011/139233 A1 | 11/2011 |
| WO | WO 2012/092163 A | 7/2012 |
| WO | WO 2013/186031 A | 12/2013 |

OTHER PUBLICATIONS

Lu, et al., "Grain Refinement in the Solidification of Undercooled Ni—Pd Alloys," Journal of Crystal Growth, 309, 2007 (9 pages).
Vecellio, L., "The mesh nebulizer: a recent innovation for aerosol delivery," Breathe, vol. 2, No. 3, Mar. 2006 (10 pages).

* cited by examiner

METHOD FOR PRODUCING AN APERTURE PLATE

RELATED APPLICATIONS

This application is a continuation of U.S. patent application Ser. No. 14/719,036, filed May 21, 2015, which claims priority to U.S. Provisional Application No. 62/002,435, filed May 23, 2014, the contents of all of which are herein incorporated by reference in its their entireties.

FIELD OF THE INVENTION

The invention relates to manufacture of aperture plates (or "vibrating membranes") for aerosol (or "nebulizer") devices.

PRIOR ART DISCUSSION

An aperture plate is used for aerosol delivery of liquid formulations in a controlled liquid droplet size suitable for pulmonary drug delivery. The ideal nebulizer is one which assures a consistent and accurate particle size in combination with an output rate that can be varied to deliver the drug to the targeted area as efficiently as possible. Delivery of the aerosol to the deep lung such as the bronchi and bronchiole regions requires a small and repeatable particle size typically in the range of 2-4 μm in general, outputs greater than 1 ml/min are required.

U.S. Pat. Nos. 6,235,177, 7,066,398 and 8,398,001 describe an approach to manufacturing an aperture plate in which a wafer is built onto a mandrel by a process of electro-deposition where the dissolved metal cations in the plating bath (typically Palladium and Nickel) are reduced using electrical current from the liquid form to the solid form on the wafer. Material is reduced only to the conducting surface on the mandrel and not to photo resist islands which are non-conducting. The aperture hole size and profile are defined by the three dimensional growth of plated materials, thus, electroforming. After the conclusion of the plating process, the mandrel/wafer assembly is removed from the bath and the wafer peeled from the mandrel for subsequent processing into an aperture plate.

However, a problem with this approach is that the wafer thickness is intertwined with the placement density of the non-conducting resist islands, i.e. the thicker the wafer, the further the distance between the non-conduction resist islands, and the smaller the aperture density. As a result, it is not possible to increase the aperture density to about 90,000 holes per square inch (approx. 650 $mm^2$). Reduced wafer thickness is Used to alleviate this issue. If a wafer has a thickness in the range of 50 to 54 μm non-standard drives are required. Also, a reduction in the aperture plate thickness alters the harmonics and natural frequency of the core assembly. To drive this optimally to generate an acceptable flow rate output, it is necessary to alter the drive frequency. This is disadvantageous as it requires the development, manufacture, and supply of a matching drive controller which has consequential cost and lead time implications.

Photo-defined technology as described in WO2012/092163A and WO2013/186031A allows a large number of holes to be produced per unit area because it applies standard wafer processing technology to define the aperture plate hole size and profile through photolithography, thus, “photo-defined”.

This technology may involve plating multiple layers to achieve desired aperture plate geometry and profile, for example, a first layer normally called the outlet or droplet size defining layer, and subsequently imparting a second layer on top of this which is normally called the inlet or reservoir layer. It can be challenging to achieve the correct levels of interfacial adhesion between both layers. And the process is more complex than that for electroforming.

US2006/0203036 describes an approach to fabricating an orifice plate in which there is plating on rings, so that plated material within the rings forms apertures which narrow to a minimum at about half their depth.

The invention is directed towards providing an improved method to address the above problems.

SUMMARY OF THE INVENTION

According to the invention, there is provided a method of manufacturing an aperture plate wafer, the method comprising providing a substrate of conductive material, applying a mask over the substrate in a pattern of columns having top surfaces, electroplating (3) around the columns, removing the mask to provide a wafer of the electroplated material with aerosol-forming holes, characterized in that, the electroplating step partially over-plates the top surfaces of the columns while leaving aerosol-forming apertures of a desired size, the columns have a height in the range of 40 μm to 70 μm.

In one embodiment, the columns have a height in the range of 55 μm to 65 μm.

In one embodiment, the column width dimension is in the range of 20 μm to 40 μm.

In one embodiment, the column width dimension is in the range of 25 μm to 35 μm.

In one embodiment, the combined aperture plate wafer thickness achieved by the column height and the height of over-plating is in the range of 50 μm to 70 μm.

In one embodiment, the aperture size is in the range of 2 μm to 6 μm.

In one embodiment, the over-plating is controlled and the column dimensions are chosen to also achieve a desired slope of wafer material towards the aerosol-forming apertures to achieve a funnelling effect for liquid in use.

In one embodiment, the wafer is formed into a dome shape which is concave on the side of the apertures, and the extent of curvature and the shape of the over-plated metal is chosen to provide a funnelling effect for liquid towards the apertures.

In one embodiment, the top surfaces of at least some columns are generally convex.

In one embodiment, the columns are configured so that when the masking material is removed they form passageways aligned with the apertures and being shaped for entrainment of droplets form the apertures.

In one embodiment, at least some of the columns have a configuration widening towards the substrate so that after removal of the masking material they form passageways which widen in a direction away from the apertures.

In one embodiment, the passageways are gradually tapered with a consistent slope.

Preferably, the passageways have a length in the range of range of 40 μm to 70 μm.

In another aspect, the invention provides an aperture plate comprising a body of metal configured with aerosol-forming apertures in a top surface and passageways aligned with and beneath the apertures, wherein the metal forms convex shapes around the apertures to provide a funnel-shaped entrance to the apertures.

Preferably, said passageways have a length in the range of 40 μm to 70 μm. In one embodiment, the passageways widen towards the lower side of the plate.

In one embodiment, the passageways have a length of 55 μm to 65 μm and the aperture plate has a thickness in the range of 50 μm to 70 μm; and wherein the passageways have a width in the range of 20 μm to 40 μm. In one embodiment, the passageways have a width in the range of 25 μm to 35 μm.

In another aspect, the invention provides an aerosol-forming device comprising an aperture plate as defined above in any embodiment, a support for the aperture plate, and a drive for the aperture plate.

According to the invention, there is provided a method of manufacturing an aperture plate wafer, the method comprising providing a substrate of conductive material, applying a mask over the substrate in a pattern of columns, electroplating the spaces around the columns, removing the mask to provide a wafer of the electroplated material with aerosol-forming holes where the mask columns were, wherein the electroplating step partially over-plates the tops of the columns while leaving aerosol-forming apertures of a desired size.

In One embodiment, the column height is chosen to achieve a desired wafer thickness.

In one embodiment, the columns have a height in the range of 40 μm to 70 μm, and preferably 55 μm to 65 μm. In one embodiment, the column width dimension is in the range of 20 μm to 40 μm, preferably 25 μm to 35 μm.

In one embodiment, the combined wafer plate achieved by the column height and the height of over-plating is in the range of 50 μm to 70 μm. Preferably, the aperture size is in the range of 2 μm to 6 μm.

In one embodiment, the over-plating is controlled and the column dimensions are chosen to also achieve a desired slope of wafer material towards the aerosol-forming apertures to achieve a funnelling effect for liquid. In one embodiment, the wafer is formed into a dome shape which is concave on the side of the apertures, and the extent of curvature and the shape of the over-plated metal is chosen to provide a funnelling effect for liquid towards the apertures.

In one embodiment, at least some columns have a generally convex top surface.

In one embodiment, the columns are configured so that when the masking material is removed they form passageways aligned with the apertures and being shaped for entrainment of droplets form the apertures.

In one embodiment, at least some of the columns have a configuration widening towards the substrate so that after removal of the masking material they form passageways which widen in a direction away from the apertures. Preferably, the passageways are gradually tapered with a consistent slope. In one embodiment, the plated metal includes Ni. In one embodiment, the plated metal includes Pd. In one embodiment, both Ni and Pd are present in the plated metal.

In one embodiment, both Ni and Pd are present in the plated metal; and wherein the proportion of Pd is in the range of 85% w/w and 93% w/w, and preferably about 89%, substantially the balance being Ni.

In one embodiment, the method comprises the further steps of further processing the wafer to provide an aperture plate ready to fit into an aerosol-terming device. In one embodiment, the wafer is punched and formed into a non-planar shaped aperture plate. In one embodiment, the wafer is annealed before punching.

In another aspect, the invention provides an aperture plate wafer comprising a body of metal whenever formed in a method as defined above in any embodiment.

In another aspect, the invention provides an aperture plate comprising a body of metal configured with aerosol-forming apertures in a top surface and passageways aligned with and beneath the apertures.

In one embodiment, the metal body forms convex shapes around the apertures to provide a funnel-shaped entrance to the apertures. In one embodiment, the passageways widen towards the lower side of the plate.

In one embodiment, the passageways are gradually tapered with a uniform sloped taper.

In one embodiment, the passageways have a length of 40 μm to 70 μm, and preferably 55 μm to 65 μm, and the aperture plate has a thickness in the range of 50 μm to 70 μm.

In one embodiment, the passageways have a width in the range of 20 μm to 40 μm, preferably 25 μm to 35 μm.

An aerosol-forming device comprising an aperture plate as defined above in any embodiment.

DETAILED DESCRIPTION OF THE INVENTION

Brief Description of the Drawings

The invention will be more clearly understood from the following description of some embodiments thereof, given by way of example only with reference to the accompanying drawings in which.

DESCRIPTION OF THE EMBODIMENTS

Figure 1:
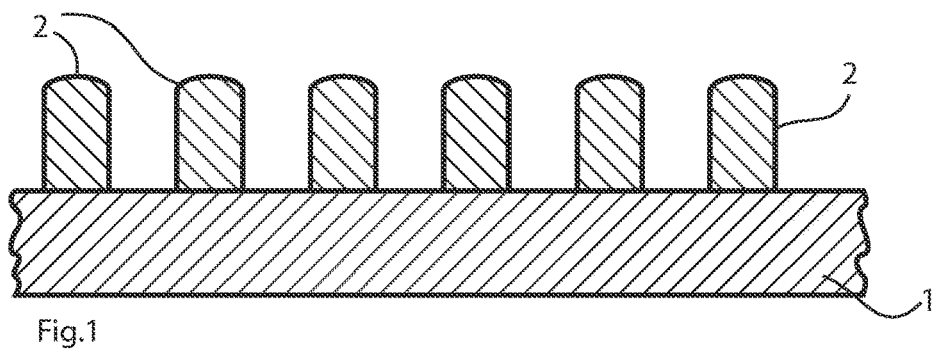
FIGS. 1 to 4 are a series of cross-sectional views showing stages of manufacturing an aperture plate.

Referring to FIGS. 1 to 4, the following are the main steps to manufacture an aperture plate in one embodiment.

An aperture plate is manufactured by plating metal around a mask of resist columns 2 having a height of about 45 μm, a diameter of about 30 μm and a separation of about 30 μm. The plating is continued so that the metal 3 overlies the top surfaces of the columns until the desired apertures 4 are achieved. This provides the benefits of both photo-defined technology (by reducing the aspect ratio near the aperture region during electroforming) and aperture density by enabling more closely patterned resist islands, with need for only one masking/plating cycle to achieve the desired plate thickness.

In more detail, non-conductive photo-resist 2 is laid on to a mandrel 1 substrate. This is developed to leave the upstanding columns 2 where holes are required. The tops of the columns 2 are approximately convex. The mandrel is placed in an electroforming tank. As the plating continues, the space between the columns 2 of developed photo resist is in-filled with the plating material. This is typically a PdNi alloy matrix, or it could alternatively be Nickel or a Nickel Cobalt alloy matrix.

Figure 2:
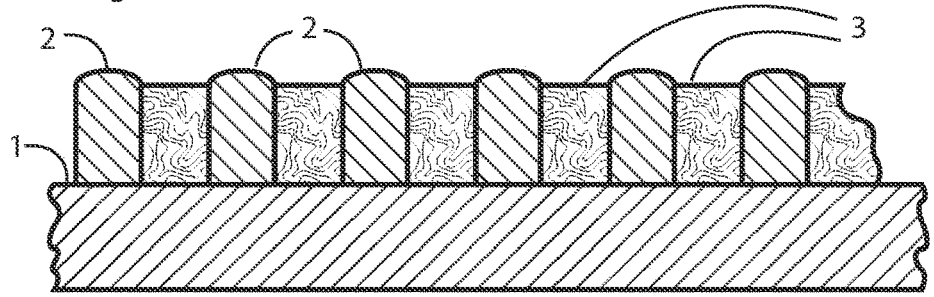
Figure 3:
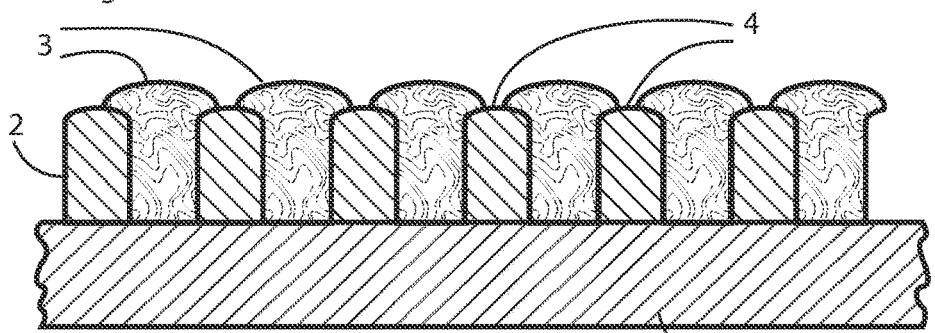

The plating is initially to the extent shown in FIG. 2 and is continued so that over-plating occurs as shown in FIG. 3. This plating is stopped just in time to create 2 to 6 μm holes 4 as shown also in FIG. 3.

The diametrical size accuracy of these holes can be improved by slowing down the plating deposition activity as the holes are being formed. This prevents 'overshoot' resulting in smaller or occluded holes with the possibility of a thicker than desired wafer construction. The 45 µm column height is so chosen such that when the plating is stopped (FIG. 3) the holes are typically 2 to 6 µm and preferably 2 to 5 µm, which is required to produce droplets in the inhalable range for nebulisation, and concurrently the wafer thickness is in the range of 60 to 62 µm in one embodiment.

Figure 4:
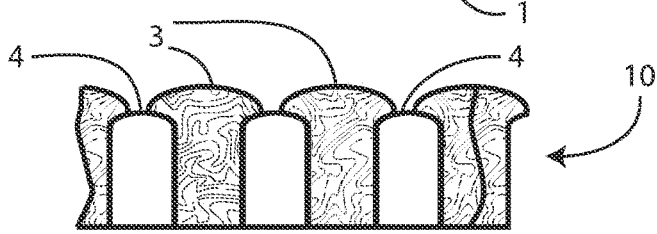

The convex shape of the entry surfaces to the apertures in addition to the concave shape of the overall domed shaped aperture plate (FIG. 7) provides effective funnelling of the liquid towards the aerosol-forming apertures 4, thereby minimising the residual volume of the drug in the nebuliser. When the photo-resist 2 is removed using an appropriate dissolving solvent, the full wafer cross-section is evident as depicted in FIG. 4. The cross-sectional profile under the hole 4 forms passageways directly under and aligned with the apertures. Because they are formed by removal of the column resist they have the same length as the heights of the columns 2. In use, these passageways under the apertures encourage entrainment of the aerosol towards the outlet of the nebuliser, thereby reducing coalescence with the resultant undesirable effect of larger droplets being formed.

Figure 5:
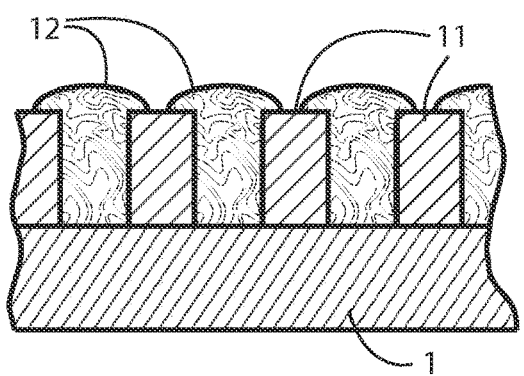
FIG. 5 is a cross-sectional view of a stage in an alternative embodiment.

In an alternative embodiment (FIG. 5), photo-resist columns 11 have flat top surfaces over which the metal (12) is plated.

Figure 6:
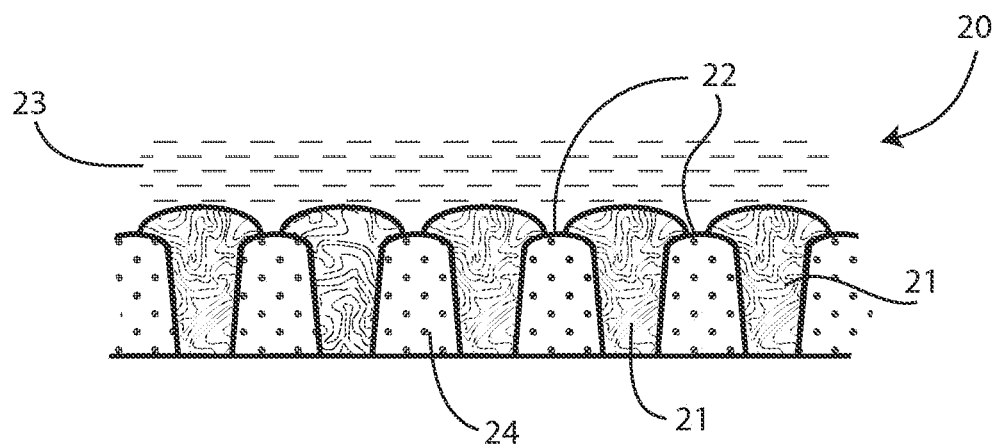
FIG. 6 is a cross-sectional diagram illustrating an alternative approach in which there are tapered openings below the aerosol-forming apertures.

As evident from FIG. 6, in a plate 20 the remaining metal may form outlet hole or passageway 24 sides that are tapered towards the aerosol outlet direction. This drawing shows the wafer metal 21 forming aerosol-forming apertures 22. The liquid 23 is aerosolized through the apertures 22 to exit as droplets through the entrainment openings or passageways 24 aligned with and below the apertures 22. Clearly, choice of geometry of the resist columns decides the geometry of the passageways.

Figure 7:
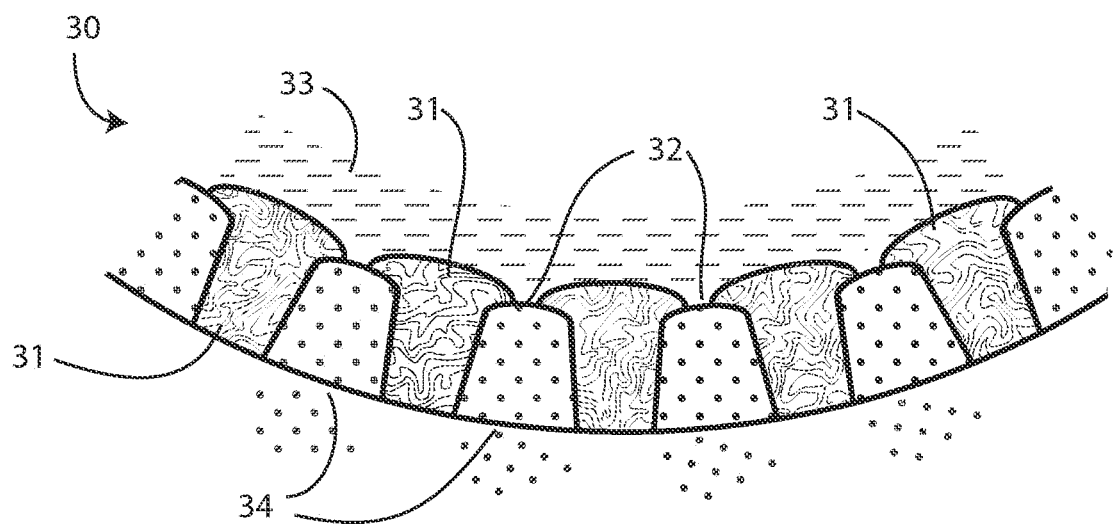
FIG. 7 shows an aperture plate of the type n FIG. 6 after it has been formed into a dome shape.

FIG. 7 shows an aperture plate 30 with metal 31 forming apertures 32 and droplet entrainment openings 34, after being formed into a dome shape. As noted above, this dome shape together with the convex shape of the metal between the apertures 32 helps to effectively funnel the liquid 33 towards the apertures 32 in order to form droplets, which exit via the entrainment openings 34.

These much larger holes 34 in comparison (to the aperture diameter) can entrain the aerosol, almost into a laminar flow pattern. This reduces turbulence and consequential coalescence which can lead to an undesirable increase in droplet size. These openings may be tapered (FIGS. 6 and 7) or not (FIGS. 1-4).

The resultant wafer 10 has a greater number of holes, greater than 44,100 per 650 mm$^2$ (square inch, Mesh 210), than the prior art and yet maintains the same aperture plate thickness (approximately 61 µm) as many commercially available products. This ensures that the existing drive controllers (128 kHz) already in situ in many hospitals can be used for the aperture plate, alleviating the cost and considerable time required to be expended to develop a bespoke drive controller to ensure that the correct frequency is available to achieve optimum aerosol output. It is also more conducive for meeting and exceeding the fatigue life requirements. As there is single-layer plating it incorporates a fine equiaxed microstructure.

It will be appreciated that the method provides the benefits of both photo-defined technology, partially decoupling the dependence of wafer thickness to resist island patterning distance and increased aperture density, with the process simplicity of electroforming, because it needs only one masking/plating cycle to achieve the desired plate thickness.

Those skilled in the electro-deposition field will appreciate how the plating conditions may be chosen to suit the circumstances, and the entire contents of the following documents are herein incorporated by reference: U.S. Pat. Nos. 4,628,165, 6,235,117, US2007023547, US2001013554, WO2009/042187, and Lu S. Y., Li J. F., Zhou Y. H., "Grain refinement in the solidification of undercooled Ni—Pd alloys", Journal of Crystal Growth 309 (2007) 103-111, Sep. 14, 2007. Generally, most electroplating solutions involving Palladium and Nickel would work or Nickel only or indeed Phosphorous & Nickel (14:86) or Platinum. It is possible that a non-Palladium wafer could be plated at the surface (1-3 microns thick) in PdNi to impart more corrosion resistance. This would also reduce the hole sizes if smaller openings were desired.

The resist geometry, such as height, width, and shape, is configured in such a way as to increase the number of holes while maintaining the desired wafer thickness. Further increase of hole density is also possible. For example, the invention in one embodiment achieves an aperture plate of about 4 times the density (moving from 210 to 420 holes per 25 mm (linear inch) or from 44,100 to 176,400 holes per 650 mm$^2$ (square inch), while still maintaining the typical 60 to 62 µm thickness range.

Adjusting the dimensions in FIG. 1, by reducing the column 2 diameter (30 µm) and dimensions between the columns 2 to say 15 µm has the potential to increase the number of holes to 700 to 850 per 25 mm (linear inch).

The invention avoids need for two-layer photo defined technology to increase the number of holes while maintaining the same wafer thickness. It also solves the problem of using standard plating defined technology as referred to in the Prior Art Discussion with a greater number of holes which will result in a lower thickness wafer, thus requiring significant changes to the core construction, or more typically the drive controller, to find the optimum drive frequency.

The invention finds particular application where faster nebulisation treatment times are required. This is usually required for hand-held devices when aerosol is administrated through the mouth or nasal passages in fully mobile patients. These are typically patients who administer nebulised drugs in a non-hospital setting.

This is in contrast to intubated hospital patients who are typically on mechanical ventilation where treatment times are less important as long as the patient gets the full prescribed dose.

Techniques for vibrating the aperture plates are described generally in U.S. Pat. Nos. 5,164,740; 5,586,550; and 5,758,637, which are incorporated herein by reference. The aperture plates are constructed to permit the production of relatively small liquid droplets at a relatively fast rate. For example, the aperture plates of the invention may be employed to produce liquid droplets having a size in the range from about 2 µm to about 10 µm, and more typically between about 2 µm to about 5 µm. In some cases, the aperture plates may be employed to produce a spray that is useful in pulmonary drug delivery procedures. As such, the sprays produced by the aperture plates may have a respirable fraction that is greater than about 70%, preferably more than about 80%, and most preferably more than about 90% as described in U.S. Pat. No. 5,758,637.

In some embodiments, such fine liquid droplets may be produced at a rate in the range from about 2 µl (microliters) per second to about 25 µl per second per 1000 apertures. In this way, aperture plates may be constructed to have multiple apertures that are sufficient to produce aerosolized volumes that are in the range from about 2 µl to about 25 µl, within a time that is less than about one second. Such a rate of production is particularly useful for pulmonary drug delivery applications where a desired dosage is aerosolized at a rate sufficient to permit the aerosolised medicament to be directly inhaled. In this way, a capture chamber is not needed to capture the liquid droplets until the specified dosage has been produced. In this manner, the aperture plates may be included within aerosolisers, nebulizers, or inhalers that do not utilise elaborate capture chambers.

The aperture plate may be employed to deliver a wide variety of drugs to the respiratory system. For example, the aperture plate may be utilized to deliver drugs having potent therapeutic agents, such as hormones, peptides, and other drugs requiring precise dosing including drugs for local treatment of the respiratory system. Examples of liquid drugs that may be aerosolized include drugs in solution form, e.g., aqueous solutions, ethanol solutions, aqueous/ethanol mixture solutions, and the like, in colloidal suspension form, and the like. The invention may also find use in aerosolizing a variety of other types of liquids, such as insulin.

It will be appreciated that the invention allows the production of a wafer from which nebuliser aperture plates are punched in one single plating step and facilitates the creation of a larger number of holes than that known today (typically up to 400%). Also, it facilitates the use of aperture plates which are 60 to 62 µm thick. Also, it allows an increase in the number of holes per unit of area while still being able to control the plating thickness to a predetermined dimension.

The above in combination allows the creation of a higher output nebuliser while still maintaining the standard drive controller and core construction all of which is accomplished in a very economical manner.

The invention claimed is:

1. A method of manufacturing an aperture plate wafer, the method comprising:
   providing a substrate,
   applying a mask over the substrate in a pattern of columns, each column having a top surface;
   electroplating a plating material around the columns at a first speed to form a first thickness;
   continuing electroplating the plating material at a second speed less than the first speed such that the plating material is over-plated to form a second thickness directly on the top surfaces of the pattern of columns so as to form a plurality of aerosol-forming apertures and wherein the first thickness is greater than the second thickness;
   removing the plated material from the mask and the substrate to provide a wafer of electroplated material with the plurality of aerosol-forming apertures;
   forming the aperture plate wafer into a dome-shape; and
   wherein a combined thickness of the first thickness and second thickness is in the range of 50 µm to 70 µm.

2. The method of claim 1, wherein the applying the mask over the substrate includes applying a first end of each of the plurality of columns to the substrate, wherein the first end includes a larger cross-sectional dimension than a second end of each of the plurality of columns.

3. The method of claim 1, wherein the columns are configured so that the removing the plated material from the mask and the substrate forms passageways aligned with the plurality of aerosol-forming apertures and being shaped for entrainment of aerosol.

4. The method of claim 1, wherein the top surfaces of the mask are rounded.

5. The method of claim 1, wherein the removing the plated material from the mask and the substrate forms a plurality of entrainment portions of the aperture plate wafer, wherein the entrainment portions are tapered.

6. A method of manufacturing an aperture plate wafer, the method comprising:
   applying a mask over a substrate in a pattern of columns, each column having a frustoconical bottom portion terminating in a convex top surface, wherein a height of each column is greater than a diameter of each column;
   electroplating a plating material around the columns at a first speed to form a first thickness;
   over-plating the plating material directly on the top surfaces of the pattern of columns at a second speed less than the first speed to form a second thickness and so as to form a plurality of aerosol-forming apertures, wherein the first thickness is greater than the second thickness;
   removing the plated material from the mask and the substrate to provide a wafer of electroplated material with the plurality of aerosol-forming apertures and tapered entrainment portions; and
   forming the aperture plate wafer into a dome-shape.

7. The method of claim 6, wherein, the wafer includes only one layer of electroplated material.

8. The method of claim 6, wherein a combined thickness of the first thickness and the second thickness is in the range of 50 µm to 70 µm.

9. The method of claim 6, wherein the plurality of aerosol-forming apertures each have a diameter in the range of 2 µm to 6 µm.

10. The method of claim 6, wherein the entrainment portions are aligned with the plurality of aerosol-forming apertures so as to form passageways extending through the wafer.

11. The method of claim 6, wherein the forming the aperture plate wafer into the dome-shape includes deflecting at least some of the plurality of aerosol-forming apertures toward one another.

12. A method of manufacturing an aperture plate wafer, the method comprising:
   applying a mask over a substrate in a pattern of columns, each column tapering to define a frustoconical bottom portion with a convex top surface, wherein a height of each column is greater than a diameter of each column;
   electroplating a plating material around the columns at a first speed to form a first thickness;
   over-plating the plating material directly on the top surfaces of the pattern of columns at a second speed less than the first speed to form a second thickness and so as to form a plurality of aerosol-forming apertures, wherein the first thickness is greater than the second thickness; and
   removing the plated material from the mask and the substrate to provide a wafer of electroplated material with the plurality of aerosol-forming apertures aligned with tapered entrainment portions;
   wherein, the wafer includes only one layer of electroplated material and wherein a combined thickness of the first thickness and the second thickness is in the range of 50 µm to 70 µm.

13. The method of claim 12, wherein the plurality of aerosol-forming apertures each have a diameter in the range of 2 µm to 6 µm.

14. The method of claim 12, wherein the entrainment portions taper towards the plurality of aerosol-forming apertures.

\* \* \* \* \*